US012753380B2

(12) United States Patent
Clary et al.

(10) Patent No.: US 12,753,380 B2
(45) Date of Patent: Oct. 6, 2026

(54) CO2-FED PHOTOBIOREACTOR

(71) Applicant: PHYCO2 LLC, Henderson, NV (US)

(72) Inventors: William B. Clary, Newburyport, MA (US); Gregory A. Hagopian, Henderson, NV (US)

(73) Assignee: PHYCO2 LLC, Henderson, NV (US)

( * ) Notice: Subject to any disclaimer, the term of this patent is extended or adjusted under 35 U.S.C. 154(b) by 411 days.

(21) Appl. No.: 18/384,925

(22) Filed: Oct. 30, 2023

(65) Prior Publication Data

US 2025/0136918 A1 May 1, 2025

(51) Int. Cl.
*C12M 1/36* (2006.01)
*C12M 1/00* (2006.01)
*C12M 1/34* (2006.01)

(52) U.S. Cl.
CPC ............ *C12M 41/48* (2013.01); *C12M 21/02* (2013.01); *C12M 41/34* (2013.01); *C12M 41/36* (2013.01)

(58) Field of Classification Search
CPC ...... C12M 41/48; C12M 41/34; C12M 41/36; C12M 31/10; C12M 31/02; C12M 31/08; C12M 31/00; C12M 31/12; C12M 43/04; C12M 43/06; C12M 43/08; C12M 21/02; C12M 23/06; C12M 23/22; C12N 1/12; C12N 1/10; C12N 1/20; C12N 13/00; C02F 3/32; C12P 5/023; C12P 7/649; A01G 33/00
See application file for complete search history.

(56) References Cited

U.S. PATENT DOCUMENTS

| | | | |
|---|---|---|---|
| 8,033,047 B2 | 10/2011 | Rasmussen et al. | |
| 8,183,032 B2 | 5/2012 | Frank | |
| 8,476,067 B2 | 7/2013 | Morgan | |
| 8,507,253 B2 | 8/2013 | Berzin | |
| 9,453,193 B2 | 9/2016 | Babbitt et al. | |
| 9,763,398 B2 | 9/2017 | Deane | |
| 10,123,495 B2 | 11/2018 | Ordway et al. | |
| 11,028,355 B2 | 6/2021 | Falco | |
| 11,371,002 B2 | 6/2022 | Jaques et al. | |
| 2009/0011492 A1* | 1/2009 | Berzin .................. | C12M 23/08 435/257.1 |

(Continued)

FOREIGN PATENT DOCUMENTS

| | | |
|---|---|---|
| CN | 114057300 | 2/2022 |
| EP | 4761847 | 6/2026 |
| WO | PCT/US2024/041962 | 8/2024 |
| WO | PCT/US2024/041977 | 8/2024 |

(Continued)

OTHER PUBLICATIONS

U.S. Appl. No. 18/951,066, William B. Clary, Machine Learning Analysis and Control of CO2-Fed Photobioreactors, filed Nov. 18, 2024.

(Continued)

*Primary Examiner* — Michael L Hobbs
(74) *Attorney, Agent, or Firm* — Polsinelli LLP

(57) ABSTRACT

Carbon dioxide containing gas is collected from a point source or atmosphere and is dried, treated, and compressed. The compressed gas is fed into an algae reactor which maintains optimal conditions for algae growth. The algae grows until it reaches sufficient density to be harvested. The harvested algae is processed and packaged for sale. Additionally, revenues may be earned by quantifying the amount of CO2 captured and sequestered by the algae and determining the carbon credit equivalent value. Byproducts may additionally be sold in addition to equipment sales and licensing.

21 Claims, 7 Drawing Sheets

(56) References Cited

U.S. PATENT DOCUMENTS

| | | | |
|---|---|---|---|
| 2011/0023565 | A1 | 2/2011 | Yanik et al. |
| 2011/0307976 | A1 | 12/2011 | Ploechinger |
| 2012/0107921 | A1 | 5/2012 | Willson et al. |
| 2013/0344574 | A1 | 12/2013 | Morgan |
| 2014/0199759 | A1 | 7/2014 | Alstyne et al. |
| 2017/0158503 | A1* | 6/2017 | Foody ........................ C12F 3/10 |
| 2020/0231925 | A1 | 7/2020 | Bashan et al. |
| 2021/0286029 | A1 | 9/2021 | Higashi et al. |
| 2022/0068436 | A1 | 3/2022 | Levin et al. |
| 2022/0306979 | A1 | 9/2022 | Erhard et al. |
| 2023/0033254 | A1 | 2/2023 | Yeh et al. |
| 2025/0002829 | A1 | 1/2025 | Roulston et al. |
| 2025/0059485 | A1 | 2/2025 | Clary et al. |
| 2025/0163358 | A1 | 5/2025 | Clary et al. |
| 2025/0230388 | A1 | 7/2025 | Clary et al. |

FOREIGN PATENT DOCUMENTS

| | | |
|---|---|---|
| WO | PCT/US2024/056403 | 11/2024 |
| WO | PCT/US25/12193 | 1/2025 |
| WO | WO2025/042613 | 2/2025 |
| WO | WO2025/096033 | 5/2025 |
| WO | WO2025/106983 | 5/2025 |
| WO | WO2025/155916 | 7/2025 |

OTHER PUBLICATIONS

U.S. Appl. No. 18/235,718, William B. Clary, Machine Learning Analysis and Control of CO2-Fed Photobioreactors, filed Nov. 18, 2024.

PCT Application No. PCT/US2024/056403, International Search Report and Written Opinion dated Jan. 16, 2025.

"Instruction guide BIOREACTOR Software 0.10.x," Photon System Instruments, pp. 1-19, retrieved from internet Jan. 8, 2025: [URL:https://psi.cz/support/downloads/pb001/sw001]. Oct. 2023.

Earl, Bill, "Calibrating Sensors," Mouser Electronics, retrieved from internet Jan. 7, 2025 [URL:https://leam.adafruit.com/calibrating-sensors], Nov. 2021.

PCT Application No. PCT/US2025/012193, International Search Report and Written Opinion dated May 21, 2025.

PCT Application No. PCT/US2024/041962, International Search Report and Written Opinion dated Oct. 25, 2024.

PCT Application No. PCT/US2024/041977, International Search Report and Written Opinion dated Oct. 25, 2024.

Dormido et al., "An Interactive Tool for Outdoor Computer Controlled Cultivation of Microalgae in a Tubular Photobioreactor System," Sensors, 14:4466-4483, 2014.

U.S. Appl. No. 19/030,460, William B. Clary, Photobioreactor Monitoring of Algae-to-CO2 Mass Ratios for Carbon Captured by Microalgae, filed Jan. 17, 2025.

PCT Application No. PCT/US2024/041962, International Preliminary Report on Patentability dated Mar. 5, 2026.

U.S. Appl. No. 18/235,718, Non-Final Office Action dated May 19, 2026.

PCT Application No. PCT/US2024/041977, International Preliminary Report on Patentability dated May 15, 2026.

PCT Application No. PCT/US2024/056403, International Preliminary Report on Patenability dated May 28, 2026.

PCT Application No. PCT/US2025/012193, International Preliminary Report on Patentability dated Jul. 30, 2026.

* cited by examiner

CO2-FED PHOTOBIOREACTOR

BACKGROUND OF THE INVENTION

1. Field of the Disclosure

The present disclosure is generally related to systems for capture of carbon dioxide-containing gases, particularly systems that use biomass to store and utilize the captured carbon dioxide.

2. Description of the Related Art

A problem related to carbon capture is the high resource cost (inefficiencies) involved in capturing, sequestering, and utilizing the captured carbon dioxide. Building the necessary infrastructure for capturing, transporting, and storing carbon dioxide can be time-consuming, energy-consuming, and otherwise costly at each stage of development—from constructing carbon capture facilities to developing pipelines or transportation systems to associated energy consumption. Furthermore, the operational costs in time, energy, and resources associated with continuous monitoring, maintenance, and storage risk for carbon capture processes further contribute to the overall difficulty in deploying and implementing new carbon capture systems. These high resource costs pose a significant challenge and barrier to entry, particularly for industries or regions with limited resources and capabilities, hindering the widespread adoption of carbon capture technologies.

Such costs and inefficiencies may arise from energy intensity and efficiency trade-offs associated with carbon capture, as many carbon capture methods (e.g., post-combustion capture) often require significant energy to operate effectively. For instance, solvent-based capture techniques necessitate heating the solvent to release the captured carbon dioxide. This energy consumption can negatively impact the overall efficiency of power plants or industrial processes, reducing their net energy output.

A further problem is the limited infrastructure for the utilization and storage of captured carbon dioxide. After the capture process, the carbon dioxide needs to be transported and securely stored to prevent its release into the atmosphere. Establishing an extensive network of pipelines, storage facilities, and suitable geological formations for long-term storage requires substantial investments and careful planning, including planning and management of storage risks. Insufficient infrastructure can result in higher costs and logistical complexities in transporting captured carbon dioxide to storage sites. Additionally, identifying suitable storage sites can be challenging due to geological considerations and potential public resistance to underground storage.

There is, therefore, a need in the art for improved systems and methods of operating algae photoreactors for capture of carbon dioxide.

SUMMARY OF THE CLAIMED INVENTION

Embodiments of the claimed invention include systems and methods of providing algae photoreactors for capture of carbon dioxide. Such capture may include collection, extraction, processing, storage, and distribution. The carbon dioxide gas may be fed into an algae reactor that maintains optimal conditions for algae growth. The algae may be allowed to grow before being harvested, processed, and packaged for sale. The process may be monitored and controlled by various sensors operating in conjunction with computing devices coupled to the devices at each processing stage.

BRIEF DESCRIPTIONS OF THE DRAWINGS

DETAILED DESCRIPTION

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

Embodiments of the claimed invention include systems and methods of providing algae photoreactors for capture of carbon dioxide. Such capture may include collection, extraction, processing, storage, and distribution. The carbon dioxide gas may be fed into an algae reactor that maintains optimal conditions for algae growth. The algae may be allowed to grow before being harvested, processed, and packaged for sale. The process may be monitored and controlled by various sensors operating in conjunction with computing devices coupled to the devices at each processing stage.

Figure 1:
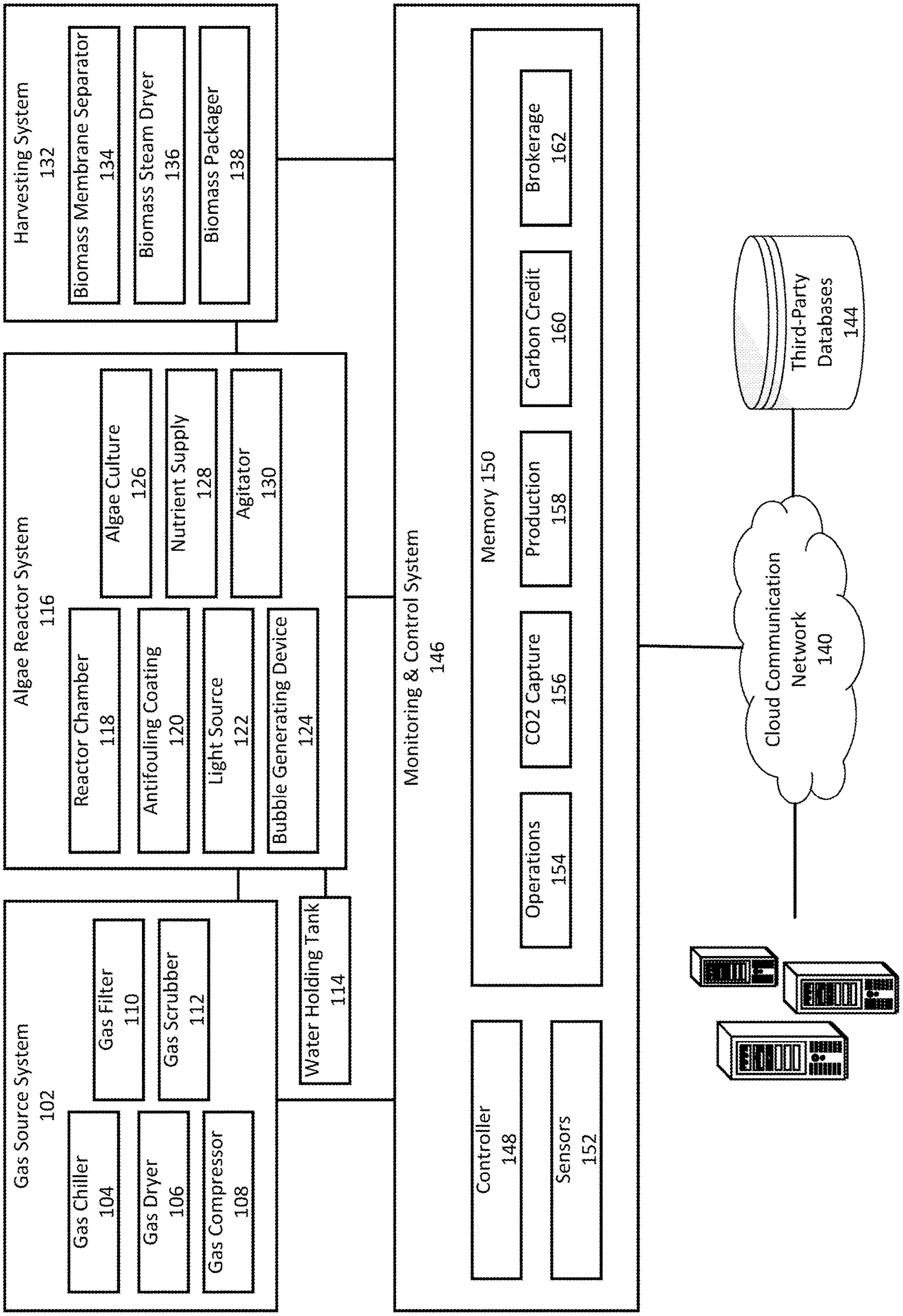
FIG. 1 illustrates an exemplary network environment in which a system for algae photoreactors for capture of carbon dioxide may be implemented.

FIG. 1 illustrates an exemplary network environment in which a system for $CO_2$ capture and biomass-based storage may be implemented. As illustrated, the network environment may include a gas collection system 102, water holding tank 114, algae reactor 116, harvesting system 132, cloud communication network 140, and monitoring and control system 146.

Gas collection system 102 may be configured to operate in conjunction with any source of gas, particularly gases containing carbon dioxide (CO2), including atmospheric or point sources. Point sources of CO2 may include industrial processes such as combustion processes, which involve the burning of fossil fuels for energy generation, heating, or other purposes. Combustion processes in power plants, refineries, and factories release CO2 as a product of the chemical reaction between fuel and oxygen. Concrete production is another significant point source of CO2 emissions. Cement, a key component of concrete, is produced through a process called calcination during which limestone (calcium carbonate) is heated to high temperatures, resulting in the release of $CO_2$ as a byproduct. Metallurgical processes such as iron and steel production release $CO_2$ as a byproduct of the reduction of iron ore using carbon (coke). Gas collection system 102 may alternatively be configured to capture exhaust gas from a fermentation process, such as the fermentation of corn to create ethanol or other biofuels, or during alcohol production, etc. Gas collection system 102 may be arranged and connected to one or more gas sources described herein using various conduits, channels, compressors, etc., for directing and controlling flow of gas. As illustrated, gas collection system 102 may include gas chiller 104, gas dryer 106, gas compressor 108, gas filter 110, and gas scrubber 112.

Gas chiller 104 first directs gas to a heat exchanger, which facilitates the transfer of heat from the gas to a cooling medium. The cooled gas may then enter a gas compressor 108, which increases its pressure for subsequent cooling and liquefaction. The gas may then be directed through a series of condensers, expansion valves, and evaporators. As the gas flows through the gas chiller 104 and exchanges heat with a refrigerant which circulates through a closed loop. The refrigerant absorbs the heat from the gas, causing it to cool down. The specific design and configuration of the gas chiller 104 depends on factors such as the volume and temperature of the gas, as well as the specific requirements of the application. Different cooling techniques, such as indirect cooling using refrigerants, are employed to achieve the desired cooling and liquefaction of the gas.

Gas dryer 106 removes water vapor from a gas, particularly a gas containing $CO_2$. In an embodiment, a gas dryer 106 may be a water dropout filter or a desiccant dryer. This type of dryer typically includes a vessel filled with a desiccant material, such as silica gel or activated alumina. The gas containing $CO_2$ is directed into the dryer vessel, where it comes into contact with the desiccant. The desiccant material has a high affinity for water molecules, so as the gas passes through the dryer, the desiccant adsorbs the moisture from the gas. This adsorption process effectively removes the water vapor, leading to a reduction in the humidity of the gas. Water removed via drying processes may be recovered for use in other processes or may be incorporated into products. The dried gas then exits the gas dryer 106. To maintain the efficiency of the drying process, desiccant dryers often include regeneration heaters or blowers, which periodically regenerate the desiccant material by heating the desiccant to remove the absorbed moisture, allowing it to be reused for subsequent drying cycles. The specific design and configuration of the gas dryer 106 may vary based on factors such as the flow rate and temperature of the gas, as well as the desired moisture content. Additionally, for larger-scale industrial applications, specialized drying systems can be employed, such as adsorption dryers or membrane dryers, which offer more advanced moisture removal capabilities.

Gas compressor 108 may include various stages or cylinders. Each cylinder contains a piston or impeller that oscillates, reducing the volume of the gas and increasing its pressure. As the piston or impeller moves, it compresses the gas within the cylinder. This compression process involves reducing the space available for the gas to occupy, causing its molecules to come closer together increasing the density and pressure of the gas. The gas is progressively compressed as it passes through multiple stages or cylinders, with each stage contributing to a further increase in pressure. Gas compressors 108 can be driven by various sources of power, such as electric motors or engines. Depending on the application, different types of compressors may be utilized, including reciprocating compressors, rotary screw compressors, or centrifugal compressors. The specific choice of compressor depends on factors such as the desired compression ratio, flow rate, and efficiency requirements. The compressed gas containing $CO_2$ can be utilized for various purposes, including storage, transportation, or further processing. Higher pressure enables more efficient storage or transport of the gas, reducing the required storage or transportation volume.

Gas filter 110 removes particulates and other contaminants from a gas stream, such as a stream of gas containing $CO_2$. Gas filter 110 may include one or more filters designed to capture undesired particles and contaminants present in the gas. The filters used may vary depending on the nature and size of the particles to be removed. Common filter types include particulate filters, bag filters, cartridge filters, electrostatic precipitators, etc. The gas filter 110 is designed with porous media that allows the gas to pass through while trapping the particulates and contaminants. These trapped particles can include dust, ash, soot, or other solid impurities present in the gas stream. The filtration process operates based on various mechanisms, such as mechanical sieving, interception, or diffusion. Larger particles are typically captured by mechanical sieving, as they are unable to pass through the small openings in the filter media. Smaller particles may be removed through interception, where they collide with and adhere to the filter fibers. Diffusion captures ultrafine particles by causing them to collide and stick to the filter media due to Brownian motion. Regular maintenance and periodic replacement of filters may be necessary to ensure optimal filtration efficiency. Over time, the filters may become clogged with captured particles, reducing their effectiveness. By replacing or cleaning the filters, the filtration system can continue to efficiently remove particulates and contaminants from the gas stream. Removing particulates and contaminants helps protect downstream equipment and processes from damage or fouling.

A gas scrubber 112 typically includes a vessel or tower filled with a scrubbing solution, such as water or a chemical reagent. The gas to be treated is directed into the scrubber, where it comes into contact with the scrubbing solution. As the gas flows through the gas scrubber 112, chemical reactions occur between the contaminants in the gas and the scrubbing solution. These reactions result in the absorption or neutralization of the contaminant chemicals or components present in the gas. The scrubbing solution acts as a medium to capture or react with the contaminants, effectively removing them from the gas. The specific design of the gas scrubber 112 can vary based on the contaminants and chemicals present in the gas. Different types of gas scrubbers 112, such as wet scrubbers or dry scrubbers, may be utilized depending on the requirements of the gas treatment process. In addition to the scrubbing solution, the gas scrubber 112 may also incorporate additional components such as filters, electrostatic precipitators, carbon absorption media, mist eliminators or demisters. These components help remove any liquid droplets or mist formed during the scrubbing process, ensuring that the treated gas leaving the gas scrubber 112 is as free from contaminants as possible. Gas scrubber 112 helps create a suitable and safe gas stream for algae cultivation.

Water holding tank 114 is a storage vessel designed to hold water received from various sources such as wells, municipal sources, water treatment facilities, or as a byproduct of industrial processes such as described herein, e.g., drying a $CO_2$-containing gas or separating water from an algae slurry. In some embodiments, the $CO_2$ rich gas may be mixed with compressed, cooled, and de-watered air before entering the water holding tank. Water holding tank 114 is typically constructed using materials that are resistant to corrosion and contamination, such as concrete, steel, or plastic. The primary function of a water holding tank 114 is to store water for later use, reuse, or to facilitate the management and distribution of water within a system such as an algae reactor 116. The water holding tank 114 is equipped with inlet and outlet connections, allowing water to enter and exit as needed. The inlet connection is connected to one or more water sources, while the outlet connection provides a means for drawing water from the tank. Water holding tank 114 may include various components such as level sensors 148 or float switches to monitor and control the water level, pressure regulators to maintain consistent water pressure, and valves for controlling the flow of water in and out of the water holding tank 114.

Water holding tank 114 operates based on the principle of maintaining a balance between water inflow and outflow. When water enters the water holding tank 114 from a source, it fills the water holding tank 114 until it reaches a predetermined level. Once the water holding tank 114 is full, the inflow is regulated, and the excess water may be redirected back to the source, to other parts of the system, or may be expelled to a drain or to the environment. In some embodiments, the water may be constitute or be incorporated into a product (such as in arid climates), treated via UV light, and/or undergo filtration using one or more filters or other purification processes to kill and/or remove bacteria and other live organisms in the water. The water may be treated to remove metals and transition elements, such as by an ion exchange filter.

An algae reactor 116, also known as a photobioreactor, is a specialized system designed to cultivate algae using a CO2-containing gas, such as a CO2-containing waste gas from an industrial process or combustion. As illustrated, algae reactor 116 may include a reactor chamber 118, antifouling coating 120, light source 122, bubble generating device 124, algae culture 126, nutrient supply 128, and agitator 130.

The algae reactor may include a reactor chamber 118 that allows light to penetrate a growth medium and supports the growth of algae. Within the reactor chamber 118, an algae slurry or suspension is maintained, which serves as the growth medium for the algae. The CO2-containing waste gas may be fed through a bubble generating device 124 which evenly disperses the CO2-containing gas into the algae slurry and may further use bubble lift processes to achieve fluid circulation and mixing while ensuring efficient contact between the CO2 and the algae cells. This CO2-containing gas serves as the carbon source for algae photosynthesis.

An algae reactor 116 may be equipped with one or more light sources 122, such as LED panels, strips, tubes, or fluorescent lamps, to provide the necessary illumination for photosynthesis. The intensity and duration of light exposure may be controlled to optimize algae growth and productivity. The algae reactor 116 may incorporate a nutrient supply 128 and/or delivery system to deliver solutions containing essential elements like nitrogen, phosphorus, and potassium, which may be added to the algae slurry to support algae growth. The nutrient concentrations may be monitored and adjusted to maintain an optimal balance for algae cultivation. The algae reactor 116 may include a temperature regulation system to maintain the desired temperature range for optimal algae growth. This may be achieved through heating or cooling mechanisms, such as heat exchangers or temperature controllers.

Reactor chamber 118 provides a controlled environment for the cultivation of algae. The reactor chamber 118 may be a sealed container or vessel and may be made of transparent material, such as glass or plastic, which may allow light to penetrate into the chamber. The algae reactor may also include metal materials, such as iron, steel, aluminum, etc. to facilitate heat transfer. The reactor chamber 118 may contain mixing mechanisms or agitators 130, such as stirrers or circulation pumps, to ensure even distribution of the algae and nutrients throughout the reactor chamber 118. The reactor chamber 118 may incorporate a light source 122 to provide the necessary illumination for photosynthesis. Light-emitting diodes (LEDs) or fluorescent lamps are commonly used to deliver the specific wavelengths and intensities of light required for optimal algae growth. The light source is positioned in a way that evenly distributes light across the algae slurry, ensuring uniform exposure for all algae cells. The light source may be located within the reactor chamber 118.

An antifouling coating 120 may prevent the attachment and growth of unwanted organisms, such as biofilms, algae, or other fouling agents, on the surfaces of the algae reactor 116 components. The antifouling coating 120 may include a specialized material or chemical formulation that inhibits the adhesion and colonization of fouling organisms. The antifouling coating 120 may be applied to the surfaces of the reactor chamber 118, including the transparent vessel, gas delivery system, and other relevant components. In some embodiments, the surfaces contacting the algae slurry possess antifouling characteristics and may not require an antifouling coating 120. An antifouling coating 120 may include biocides or antimicrobial agents. These agents may be incorporated into the coating formulation and may release over time to deter the growth of microorganisms and algae. The biocides act by disrupting cellular processes or inhibiting the colonization of fouling organisms, thereby preventing their attachment and growth on the coated surfaces. An antifouling coating 120 may modify surface properties such as surface energy or roughness, to create an unfavorable environment for fouling organisms. For example, hydrophobic coatings can reduce the ability of waterborne organisms to adhere to the surface, making it more difficult for them to establish and grow.

An algae reactor 116 may also be equipped with one or more light sources 122, such as LED panels, strips, tubes, or fluorescent lamps, to provide the necessary illumination for photosynthesis. The intensity and duration of light exposure may be controlled to optimize algae growth and productivity. A light source 122 provides the necessary illumination for photosynthesis, supporting the growth and productivity of the algae. The light source 122 in an algae reactor may emit specific wavelengths of light that are optimal for photosynthetic activity. LED panels or fluorescent lamps are commonly used as light sources due to their energy efficiency and controllable light spectrum. These light sources 122 can be positioned around and/or within the reactor to ensure uniform distribution of light throughout the algae slurry. The light source 122 operates based on the principle of converting electrical energy into light energy. In the case of LEDs, electric current passes through a semiconductor material, causing the release of photons that generate light. Fluorescent lamps work by passing an electric current through a gas-filled tube, which results in the excitation of mercury atoms and the subsequent emission of ultraviolet light. This ultraviolet light is then converted into visible light through a phosphor coating on the inner surface of the lamp. The intensity and duration of light exposure in the algae reactor may be controlled to optimize algae growth and productivity. Light intensity may be adjusted by controlling the power supply or dimming capabilities of the light source and cycling the light for certain periods and durations either with a sign wave or square wave profile. Additionally, timers or programmable controllers may be used to regulate the duration and timing of light exposure, simulating day and night cycles to maintain proper growth conditions for the algae or in an alternate pattern and/or frequency to optimize algae growth.

A bubble generating device 124 facilitates efficient gas-liquid contact between the CO2-containing waste gas and the algae slurry by dispersing bubbles of the gas within the algae culture 126 to enhance the transfer of CO2 to the algae cells. The bubble generating device 124 may additionally act to cool the liquid via the injection of cool bubbles. The bubble generating device 124 typically may include a microbubbler, diffuser, or membrane, which produces fine bubbles. A CO2-containing gas may flow through the microbubbler encountering small pores or perforations in the material, causing the gas to be released in the form of numerous small bubbles. These bubbles rise to the surface of the algae slurry, creating a gas-liquid interface where the CO2 can be efficiently absorbed by the algae cells. In some embodiments, at least some of the CO2 is solubilized into the water of the algae slurry. The rising action of the bubbles may additionally perform the function of agitating the algae. The bubble generating device 124 may include a distribution system to ensure even dispersion of the bubbles throughout the algae slurry.

An algae culture 126 is a population of algae cells which are prepared for growth within an algae reactor 116. The algae culture in algae reactor 116 is typically maintained as an algae slurry or suspension. The slurry contains water, nutrients, and the algae cells. The water serves as the medium for supporting algae growth, providing the necessary environment for their survival and reproduction. The algae culture 126 may be processed to remove microorganisms, such as via use of UV light, and other harmful elements, which may inhibit algae growth or compromise the efficiency of algae growth in an algae reactor 116.

The algae reactor 116 may incorporate a nutrient supply 128 and/or delivery system to deliver solutions containing essential elements like nitrogen, phosphorus, and potassium which may be added to the algae slurry to support algae growth The nutrient concentrations may be monitored and adjusted to maintain an optimal balance for algae cultivation. The algae reactor 116 may include a temperature regulation system to maintain the desired temperature range for optimal algae growth. This may be achieved through heating or cooling mechanisms, such as heat exchangers or temperature controllers. The reactor chamber 118 may incorporate a light source 122 to provide the necessary illumination for photosynthesis. Light-emitting diodes (LEDs) or fluorescent lamps are commonly used to deliver the specific wavelengths and intensities of light required for optimal algae growth. The light source is positioned in a way that evenly distributes light across the algae slurry, ensuring uniform exposure for all algae cells. The light source may be located within the reactor chamber 118.

A nutrient supply 128 provides the necessary elements for the growth and metabolic processes of the algae culture 126. The nutrient supply 128 may include a controlled delivery of essential nutrients to the algae slurry which may include nitrogen (N), phosphorus (P), potassium (K), and other trace elements. The nutrient supply 128 may include nutrient solutions and/or additives that contain predetermined concentrations of nutrients. The nutrient supply 128 may include reservoirs or tanks that hold the nutrient solutions, dosing pumps and/or injectors that deliver the nutrients into the algae slurry, and monitoring devices to ensure control of nutrient concentrations. The dosing pumps and/or injectors may be programmed to deliver the nutrients at specific intervals or according to a predetermined schedule. The nutrient supply 128 system may additionally incorporate sensors 152 to monitor and adjust nutrient levels. An example of a nutrient supply 128 may include a pH supply and/or delivery system to deliver solutions containing essential ions and buffers to maintain a pH level which may be added to the algae slurry to support algae growth. In an embodiment, a nutrient supply may include a chelating supply and/or delivery system to deliver solutions containing essential chemical components and ions to reduce the metals and nutrients from the algae cell walls during harvesting and to support algae growth.

An agitator 130 mixes and circulates the algae slurry, facilitating an even distribution of algae throughout the growth medium. The agitator 130 may include a motor or drive unit, which provides the necessary rotational force for the agitator. The motor may be connected directly, or indirectly via a shaft to one or more impellers or blades. The impellers or blades create turbulence and induce fluid motion within the algae reactor, ensuring uniform distribution of nutrients, gases, and light exposure to the algae culture 126. The shape and arrangement of the impellers may vary. The agitator 130 helps distribute nutrients evenly, ensuring uniform growth and preventing nutrient depletion or buildup in certain areas of the reactor. In some embodiments, the agitator 130 may not include a physical mechanism, but instead the effect may be achieved via the rising action of bubbles of CO2-containing gas through the algae slurry.

A harvesting system 132 separates the algae biomass from the liquid medium and may utilize mechanical centrifuge, membranes, settling zones or baffles to increase the concentration of the algae cells. The algae slurry may be allowed to rest or undergo gentle agitation, which promotes the settling of algae cells to the bottom of the vessel. As the algae cells settle, a concentrated layer of biomass forms, while the liquid phase (supernatant) containing water and other components is decanted or drained off. The concentrated algae biomass may be further dewatered using techniques such as filtration, centrifugation, or flocculation. Filtration involves passing the algae slurry through a filter medium that retains the algae cells while allowing the liquid to pass through. Centrifugation utilizes centrifugal force to separate the denser algae cells from the liquid phase. Flocculation involves the addition of chemical agents to induce the clumping of algae cells, facilitating their precipitation and separation from the liquid. As illustrated, harvesting system 132 may include biomass membrane separator 134, biomass steam dryer 136, and biomass packager 138.

In some implementations, the algae slurry is removed from the algae reactor 116 and most of the water is removed via the use of a biomass membrane separator 134. The water content of the algae may further be reduced via the use of a biomass steam dryer 136. A biomass membrane separator 134 may include a semi-permeable membrane having specific pore sizes that allow for the passage of liquid, dissolved substances, and smaller molecules while retaining the larger algae cells and biomass. The liquid phase, which contains water and smaller dissolved molecules, passes through the membrane and the water may be recovered and stored in a water holding tank 114. Recovered water may be reused in other processes such as in the algae reactor 116 or may be sold as a product. Via a combination of size exclusion and molecular sieving the algae cells, which are larger in size, are unable to pass through the small pores or openings of the membrane, while allowing the liquid components can permeate through the membrane structure due to their smaller size. The biomass membrane separator 134 may incorporate additional mechanisms such as backwashing or crossflow filtration. Backwashing involves periodically reversing the flow direction across the membrane surface to dislodge and remove accumulated particles and debris. Crossflow filtration utilizes a tangential flow of liquid across the membrane surface, preventing the buildup of fouling materials and maintaining optimal filtration performance.

A biomass steam dryer 136 may include a drying chamber or vessel, a steam generator, and a heat exchanger. The harvested algae biomass is introduced into the drying chamber, which is designed to facilitate the drying process. The steam generator generates high-pressure steam, which raises the temperature within the drying chamber, facilitating the evaporation of moisture from the algae biomass. As the algae biomass is exposed to the heated environment, the moisture within the cells begins to vaporize and then condenses on the cooler surfaces within the drying chamber, such as condensation plates or heat exchange coils before being collected and removed from the system. The drying process continues until the desired moisture content is achieved, resulting in a dry and concentrated algae biomass product. The dried biomass can then be further processed or utilized for various applications.

A biomass packager 138 may include a packaging machine or system, which may be automated or semi-automated and may include a conveyor belt, feeding mechanism, weighing system, and sealing apparatus The harvested algae biomass is fed into the biomass packager 138 by a conveyor belt or feeding mechanism. The algae is weighed to determine the desired packaging weight or quantity and is then deposited into the packaging material, such as bags or containers. The biomass packager 138 seals the package using any of heat sealing, adhesive sealing, or other mechanisms to ensure proper closure and preservation of the algae biomass. The packaging may include any of bulk packaging, individual bags, or containers of varying sizes.

A cloud communication network 140 may include a network of remote servers that are interconnected and provide various services and resources over the Internet. Cloud communication network 140 may include network infrastructure, servers, storage systems, and software applications. The network infrastructure allows for seamless connectivity and communication between the algae reactor and the cloud communication network 140 servers. The servers host the necessary software applications and algorithms required for data processing, analysis, and control. The storage systems provide secure and scalable storage capacity for data generated by the algae reactor. Cloud communication network 140 may facilitate remote control and management of an algae reactor. Operators may access a cloud-based control panel or dashboard to monitor and adjust various parameters of the reactor, such as CO2 flow rate, nutrient, pH, chelating agent concentration, algae density, temperature, electricity consumption, and lighting conditions. Cloud communication network 140 also enables the storage and retrieval of historical data, analysis, and future optimization of the algae reactor 116 performance. As illustrated, cloud communication network 140 may further allow for communication with third-party network servers 142 and third-party databases 144.

A third-party network server 142 may be inclusive of an external network or platform that is utilized to enable functionality and capabilities of the algae reactor 116. A third-party network servers 142 may offer various services, data analysis tools, and/or additional data or resources to optimize the algae cultivation process and improve CO2 utilization. A third-party network servers 142 may include a cloud-based platform, data analytics tools, and external APIs (Application Programming Interfaces). Data analytics tools within the third-party network servers 142 may enable advanced data processing and insights generation. These tools may employ algorithms and machine learning techniques to analyze the data collected from the algae reactor to provide valuable insights into such as CO2 consumption rates, optimal nutrient dosage, growth patterns, and other performance indicators. These insights can be used to optimize the operation of the algae reactor 116, improve CO2 utilization efficiency, and improve overall productivity. Furthermore, the third-party network servers 142 may offer external APIs that allow seamless integration between the algae reactor and external systems or services. These APIs enable data exchange and interoperability, facilitating collaborations with environmental monitoring agencies and/or industry partners including validation of carbon collected and stored within the produced algae biomass.

A third-party database 144 is any external database which may store data including operational parameters, environmental conditions, growth metrics, and historical records relating to an algae reactor. The third-party database 144 may store data related to growth characteristics of an algae culture 126 created by a vendor who prepares algae cultures 126. Similarly, a third-party database 144 may include manufacturer information relating to any component of an algae reactor 116 including gas collection and biomass harvesting.

Figure 7:
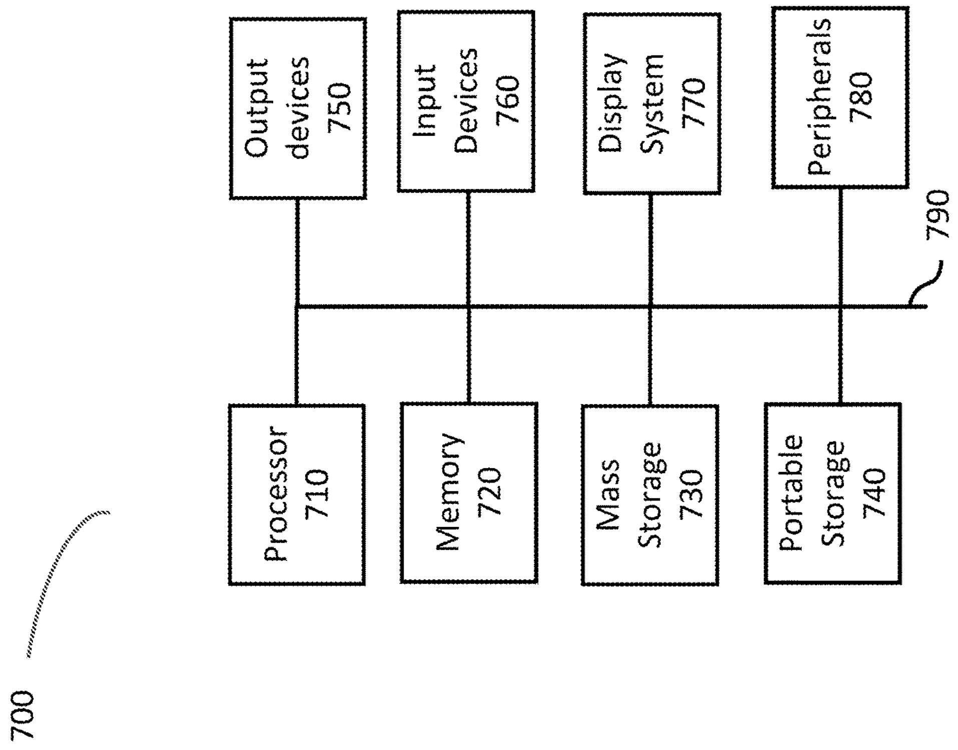
FIG. 7 is a block diagram of an exemplary computing device that may be used to implement an embodiment of the present invention.

A monitoring and control system 146 for an algae reactor 116 may be inclusive of a computing device, such as described in detail in relation to FIG. 7. Monitoring and control system 146 may include or be in communication with controller 148, memory 150, and sensors 152 within the algae reactor 116. The sensors 152 measure parameters such as CO2 concentration, temperature, pH level, dissolved oxygen, nutrient levels, etc. The sensors 152 may continuously collect data, providing real-time information about the status of the algae reactor 116. The collected data from the sensors 152 may be transmitted to a central control unit or system. The control unit processes and analyzes the data and may modify one or more parameters of an algae reactor 116 in response to the data collected from one or more sensors 152. For example, the monitoring and control system 146 may control the flow rate of the CO2-containing waste gas, adjust the lighting intensity and duration, regulate the nutrient dosing, monitor the overall conditions of algae reactor 116, etc. The control unit may further communicate with a user interface which displays sensor 152 readings and other relevant information.

The monitoring and control system 146 may additionally or alternatively include algorithms and instructions executable to perform carbon credit (e.g., carbon credit 160) and brokerage and/or arbitration (e.g., brokerage 162) functions. For example, the monitoring and control system 146 may determine the amount of CO2 captured by harvested algae biomass and may further determine a carbon credit value and/or facilitate transactions involving the algae biomass, associated carbon credits, process byproducts, or other products and services related to an algae reactor 116 including equipment and/or licensing, maintenance and/or operational services, etc.

A controller 148 may include a processor for performing computations and communicates with a memory 150 for storing data (including executable instructions or algorithms). The controller 148 may be in communication with a communications interface and/or one or more sensors 152 and may further be allowed to control the at least one function or process related to an algae reactor 116 and/or the brokerage and/or arbitration of products and/or services related to an algae reactor 116. The controller 148 may be a commercially available central processing unit (CPU) or graphical processing unit (GPU) or may be a proprietary, purpose-built design. More than one controller 148 may operate in tandem and may be of different types, such as a CPU and a GPU. A GPU is not restricted to only processing graphics or image data and may be used for other computations.

Controller 148 may execute a variety of control processes, rules, algorithms, software, services, APIs, etc., stored in memory 150 for control operations 154, CO2 capture 156, production 158, carbon credit 160, and brokerage 162. Controller 148 (such as the processor described in further detail in relation to FIG. 7) may execute associated control processes 154-162 to perform the functions described herein. Controller 148 may make calls to and initiate specific functions associated with the control processes 154-162 as needed, e.g., in response to specific calls, triggers, thresholds, determinations, etc. The controller 150 initiates the gas (CO2) capture control processes 156, which are executed to collect a CO2-containing gas and process the gas such as by chilling, drying, and compressing the gas prior to transport and/or storage. The CO2-containing gas may additionally be filtered and/or treated to remove particulates, chemicals, and other contaminants. The compressed CO2-containing gas is received, and the reactor preparation control processes 154 are initiated and executed. The algae reactor 116 may also be instructed to prepare reactor surfaces, such as via sterilization and/or application of an antifouling coating. The monitoring and control system 146 is initialized and the algae reactor 116 is filled with a medium, such as water, and an algae culture 126. A reactor status is received and the algae growth control processes 156 are executed to provide a compressed CO2 gas to the algae reactor 116.

Memory 150 is the electronic circuitry within a computing device that temporarily stores data for usage by the controller 148. The memory 150 may additionally include persistent data storage for storing data used by the controller 148. The memory 150 may be integrated into a controller 148 or may be a discrete component. The memory 150 may be integrated into a circuit, such as soldered on component of a single board computer (SBC) or may a removable component such as a discrete dynamic random-access memory (DRAM) stick, secure digital (SD) card, flash drive, solid state drive (SSD), magnetic hard disk drive (SSD), etc. In some embodiments, memory 150 may be part of a controller 148. Multiple types of memory 150 may be used.

Sensors 152 collect data by measuring one or more physical properties such as CO2 concentration, temperature, pH level, dissolved oxygen, algae density, and nutrient levels, etc. CO2 sensors 152 are essential for measuring the concentration of CO2 in the algae reactor 116 and may utilize infrared or electrochemical technology to detect and quantify the CO2 concentration in the gas phase by measuring the absorption or electrical properties of a gas sample and converting it into a CO2 concentration value. Temperature sensors 152 may include thermocouples, resistance temperature detectors (RTDs), optical temperature sensors, etc. pH sensors 152 monitor the acidity or alkalinity of an algae slurry and may utilize pH-sensitive electrodes and/or indicators that generate electrical signals corresponding to the hydrogen ion concentration in the liquid medium. Nutrient sensors 152 may monitor the levels of essential nutrients such as nitrogen, phosphorus, and potassium within the algae reactor 116.

One or more sensors 152 are polled for reactor status and measurements, which may be used to determined if adjustments to the levels of any of CO2, nutrients, water, etc., may be necessary. Further, it may be determined whether the algae is ready for harvest, and an algae growth status is received. If the algae is not ready for harvest and the reactor status is nominal, then initiate the algae growth control processes 156. If the algae is ready for harvest, the harvesting control processes 158 is initiated and executed to obtain harvest data including a processing procedure and/or parameters for a processed algae. The algae slurry is collected, and water is separated such as by using a biomass membrane separator 134 and/or a biomass steam dryer 136. The dried algae is measured, packaged, and prepared for shipment. A harvest status is received and when complete, the CO2 capture, algae growth, and harvest system is ended.

Instructions and algorithms for operations 154 may be executed by controller 148 to coordinate initiation (e.g., sequentially) of the CO2 capture 156, production 158, carbon credit 160, and brokerage 162 functions. The CO2 capture module 156 may be executed to control and coordinate the collection of a CO2-containing gas from one or more gas source systems 102 and associated processing. The production module 158 may be executed to control and coordinate the utilization of the CO2-containing gas—following collection and processing by CO2 capture module 156—to grow algae in an algae reactor 116. The carbon credit module 160 may be executed by controller 148 to determine the net amount of CO2 sequestered in the algae and further calculate the carbon credit equivalent value of the sequestered CO2. The brokerage module 162 may be executed by controller 148 to determine parameters and terms of a predetermined set of rules (e.g., stored in memory 150) associated with one or more clients to automatically initiate and/or conduct transactions involving products and/or services related to algae reactor 116 including associated algae, carbon credits, byproducts such as water, oxygen, nitrogen, etc. or alternatively, equipment purchase, lease, rent, and/or service and/or licensing. Different automated workflows may be associated with different clients, and each workflow may continue to be executed until the associated transaction is determined to have been fulfilled (e.g., in accordance with the stored rules).

In exemplary implementations, the CO2 capture module 156 may collect a CO2-containing gas from a point source such as the exhaust of an industrial process, polls sensors 152, and determines whether the CO2-containing gas requires treatment, and treats the CO2-containing gas such as via a gas chiller 104, gas dryer 106, gas compressor 108, gas filter 110, gas scrubber 112, etc. The captured CO2-containing gas is sent to the operations module 154 to be used by the production module 158 to grow algae. The CO2 capture module 156 collects a CO2-containing gas from a point source such as the exhaust of an industrial process, polls sensors 152 and determines whether the CO2-containing gas requires treatment, and treats the CO2-containing gas such as via a gas chiller 104, gas dryer 106, gas compressor 108, gas filter 110, gas scrubber 112, etc. The captured CO2-containing gas is sent to the operations module 154 to be used by the production module 158 to grow algae. The carbon credit module 160 receives an amount of algae biomass produced by the production module 158 from the operations module 154. The amount of CO2 captured by the received algae biomass is determined, in addition to the amount of CO2 produced via the process of capturing the CO2-containing gas and utilizing it to grow the algae biomass, and a net amount of CO2 captured is calculated. The current carbon credit value is retrieved and used to determine the net carbon credit value of the algae biomass which is sent to the operations module 154. The brokerage module 162 receives a carbon credit value of the algae biomass and optionally receives a product request. An offer price, or amount at which a product and/or service related to an algae reactor 116 is to be sold, is calculated and an offer is presented to one or more potential customers. If not immediately accepted, the price and/or terms of an agreement may be iteratively negotiated until an acceptance of an offer is received. The agreement or contract is fulfilled, and the contract status is sent to the operations module 154.

Figure 2:
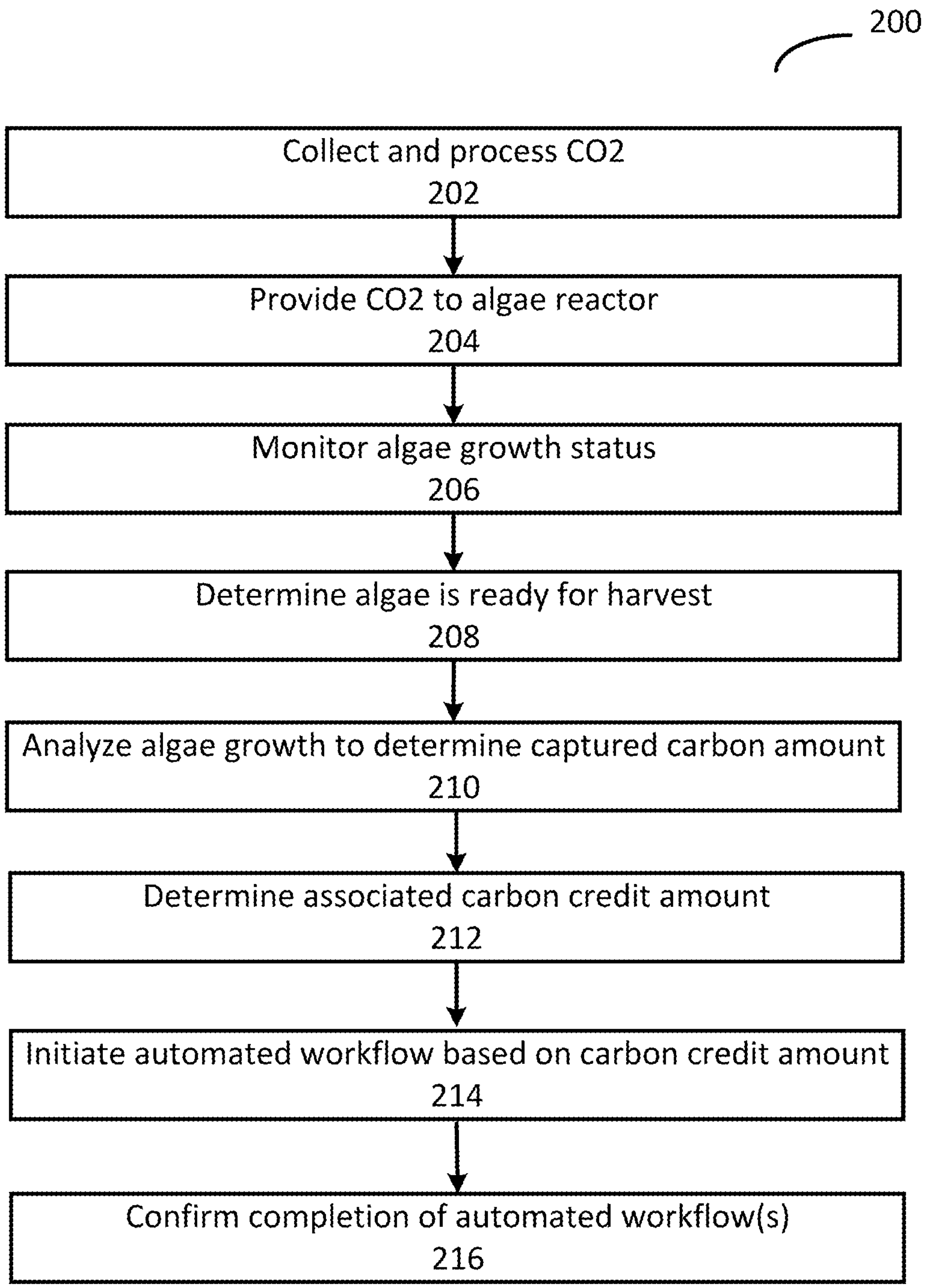
FIG. 2 is a flowchart illustrating an exemplary method of operating algae photoreactors for capture of carbon dioxide.

FIG. 2 is a flowchart illustrating an exemplary method 200 of operating algae photoreactors for capture of carbon dioxide. The method 200 may result from execution of the operations module 154 by controller 148 2. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

As illustrated, method 200 may begin with step 202 in which the CO2 capture module 156 is executed to initiate collection and processing of CO2-containing gas. The CO2 capture module 156 may coordinate collection of a CO2-containing gas from at least one point source and may optionally poll one or more sensors 152 to determine whether the CO2-containing gas requires treatment. If treatment is required, the CO2-containing gas is treated with one or more of a gas chiller 104, gas dryer 106, gas compressor 108, gas filter 110, gas scrubber 112, etc. In some embodiments, the CO2 capture module 202 may use CO2 capture methods such as temperature swing cycle or pressure swing cycle carbon capture methods to collect a concentrated CO2 gas.

At step 204, the collected and processed CO2-containing gas may be provided to algae reactor system 116, which may be associated with execution of the production module 158 to coordinate introduction of the CO2-containing gas to the algae reactor 116. Nutrients may additionally be added and sensors 152 polled to determine whether more CO2 or nutrients are required or other parameters such as temperature, light intensity, etc. need to be adjusted.

In step 206, the sensor 152 data may be used to monitor algae growth status and to determine whether the algae is ready for harvest. If the algae is ready for harvest, it is harvested; otherwise, CO2 may continue to be added to the algae reactor 116 whereby the growth process of the algae (and associated carbon capture) is allowed to continue. The algae may also continue to be monitored and measured to determine real-time status.

At step 208, the algae produced and measured by the production module 158 may be determined to be ready for harvest in accordance with predetermined rules stored in memory 150. Harvesting the algae may further include processing such as removing water from the algae. In an embodiment, receiving an amount of 1500 kg of algae biomass dried to 5% water content.

At step 210, the carbon credit module 160 may be executed to analyze the amount of algae biomass produced and determines the amount of CO2 captured by the algae. The carbon credit module 160 further may determine the amount of CO2 produced to grow the algae biomass, as well as a net amount of CO2 captured by the algae reactor 116. The current carbon credit value may therefore be determined based on the amount of captured CO2 indicated for the algae biomass.

At step 212, the carbon credit value for an amount of algae biomass produced in accordance with current rates and applicable formulas. In some implementations, different real-time rates and formulas may be determined to be applicable to the current batch of captured carbon associated with the algae biomass. The carbon credit may be measured by different measurements systems and currencies (or currency equivalents), such as USD, of the total amount of CO2 sequestered in the algae biomass based upon a carbon credit value on a carbon credit exchange, which may be represented as a dollar amount per metric ton, or a transaction amount including a specific value amount per specific amount of CO2.

At step 214, the brokerage module 162 may be executed to initiate automated workflows associated with transactions based on the carbon credit value and requests for a product and/or service. Such workflows may include evaluating a plurality of possible transaction parameters or agreement terms including any of carbon credit purchase, equipment purchase, equipment lease, product purchases such as algae, oxygen gas, water, etc., from which an agreement may selected, further negotiated, accepted, and processed by one or more of the automated workflows in accordance with applicable rules and parameters. Such automated workflows may include coordinating transfer or distribution of one or more of the products or services, updating records related to the same, and coordinating upstream processes so as to fulfill requirements of the transactions.

At step 216, a workflow status may be monitored by the brokerage module 162 to determine status. The workflow status may be indicated as pending, accepted but awaiting fulfillment, completed, etc. The workflow may terminate when the requirements of the transactions (e.g., as defined by applicable rules and parameters) are determined to have been fulfilled, met, or completed.

Figure 3:
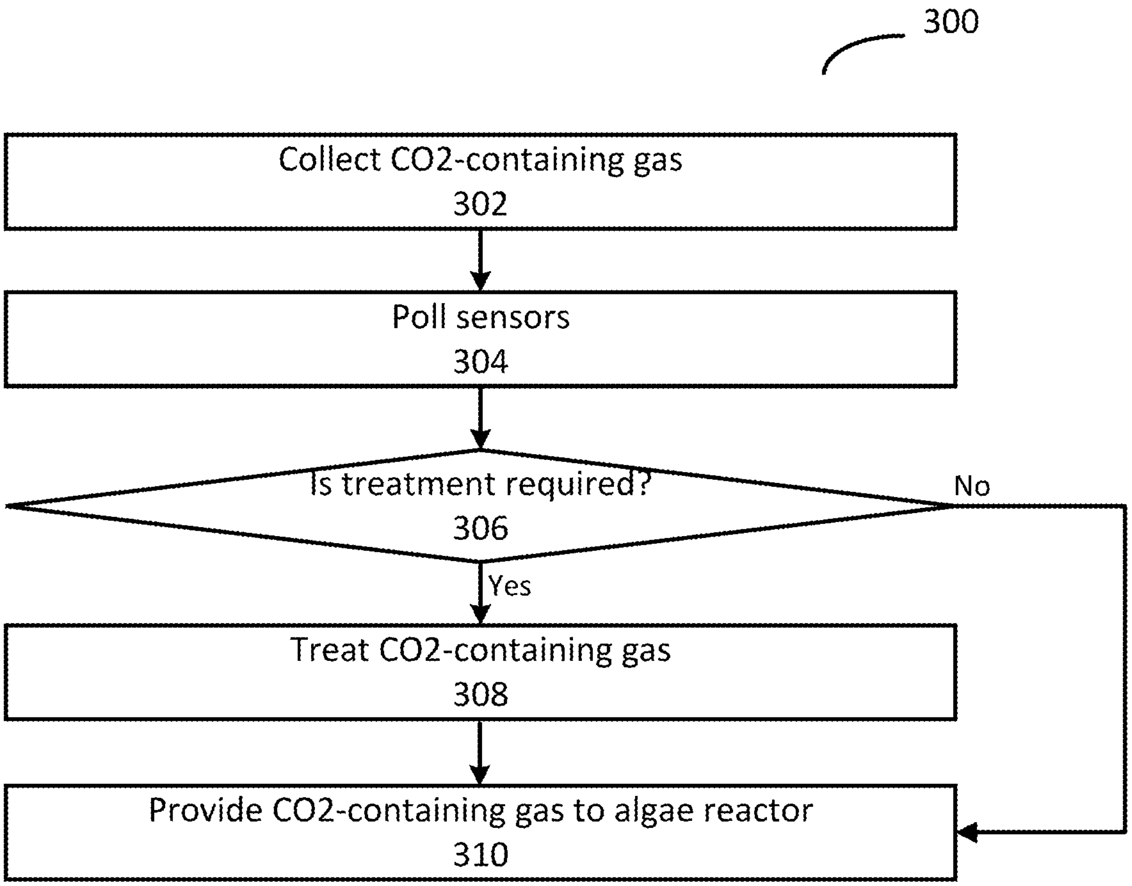
FIG. 3 is a flowchart illustrating an exemplary method of CO2 collection and processing.

FIG. 3 is a flowchart illustrating an exemplary method 300 of CO2 collection and processing. Method 300 may be performed based on execution of CO2 capture module 156 by controller 148. As noted herein, CO2 capture module 156 may include algorithms and instructions executable to coordinate and control operations of gas source system 102 including the various components 104-112 thereof.

Method 300 may begin with step 302, in which a CO2-containing gas may be collected. Such collection may include installation and use of CO2 capture apparatus, which may be configured to receive a CO2-containing gas from a gas source 102, preferably from an industrial point source such as from an energy production facility utilizing combustion, concrete production plant, fermentation processes, metallurgy, etc. A CO2-containing gas may be collected from at least one gas source 102, such as from the exhaust of an industrial process. In exemplary implementations, CO2 may be captured utilizing one or more processes such as a pressure swing cycle or temperature swing cycle carbon capture process to collect a concentrated CO2 gas. In some instances, the collected CO2-containing gas may be largely free of contaminants, while in others, the CO2-containing gas may include a high moisture content, as well as one or more contaminants that may require remediation prior to use in a bioreactor. The collected CO2-containing gas may be at ambient temperature or at a temperature substantially higher than ambient, such as 200° F. In an embodiment, the CO2-containing gas is the exhaust from the combustion of methane.

At step 304, one or more sensors 152 may be polled and instructed to measure one or more parameters of a CO2-containing gas. The parameters of the CO2-containing gas may be any of CO2 concentration, temperature, humidity or moisture content, pressure, molecular composition of component gases, presence and/or of particulates, etc. In an embodiment, the sensors 152 may measure the concentration of CO2 (e.g., 30%) and/or the temperature of the CO2-containing gas (e.g., 200° F.).

At step 306, it may be determined as to whether the CO2-containing gas requires treatment or not. If so, the method 300 may proceed to step 308, in which the CO2-containing gas may be treated. Treatment may include any type of gas treatment process, including cooling in a gas chiller 104, removing moisture via a gas dryer 106, removal of particulates and/or contaminants via one or more gas filters 110, removal and/or remediation of one or more chemical contaminants via one or more gas scrubbers 112, or compression of the CO2-containing gas.

For example, the CO2-containing gas may have a humidity of 40%, while a target humidity of less than 10% is desired; the CO2-containing gas may therefore be subject to treatment via a gas dryer 106. In another example, the CO2-containing gas may include at least one of nitrogen oxides or sulfur oxides, therefore triggering treatment via one or more gas scrubbers 112. In instances where soot is identified as being present in the CO2-containing gas, treatment may be administered via use of one or more gas filters 110 to filter the soot. Similarly, where the temperature is measured at 200° F. and the desired target temperature is less than 100° F., the CO2-containing gas may therefore be subject to treatment via a gas chiller 104. In some implementations, the CO2-containing gas may be identified as being at less than 100° F., having a humidity of 9%, and containing no chemical or particulate contaminants; thus, the CO2-containing gas may be determined to not require any treatment.

If more than one treatment is required, the treatments may occur in any order. In some embodiments, the same treatment may be performed multiple times, such as reducing the humidity of the CO2-containing gas via a gas dryer 106 from 40% to 20%, treating the gas via a gas scrubber 112 to remove nitrogen oxides, then drying the gas again to further reduce the humidity to 5%. Water and/or component gases and/or materials removed from the CO2-containing gas may be collected and utilized elsewhere in the algae growth process or may alternatively be available as a product for sale. For example, collected water may be supplied to one or more customers, particularly if the region in which the water is collected is arid.

At step 310, the CO2-containing gas may be provided to algae reactor 116 for capture by the algae biomass therein.

Figure 4:
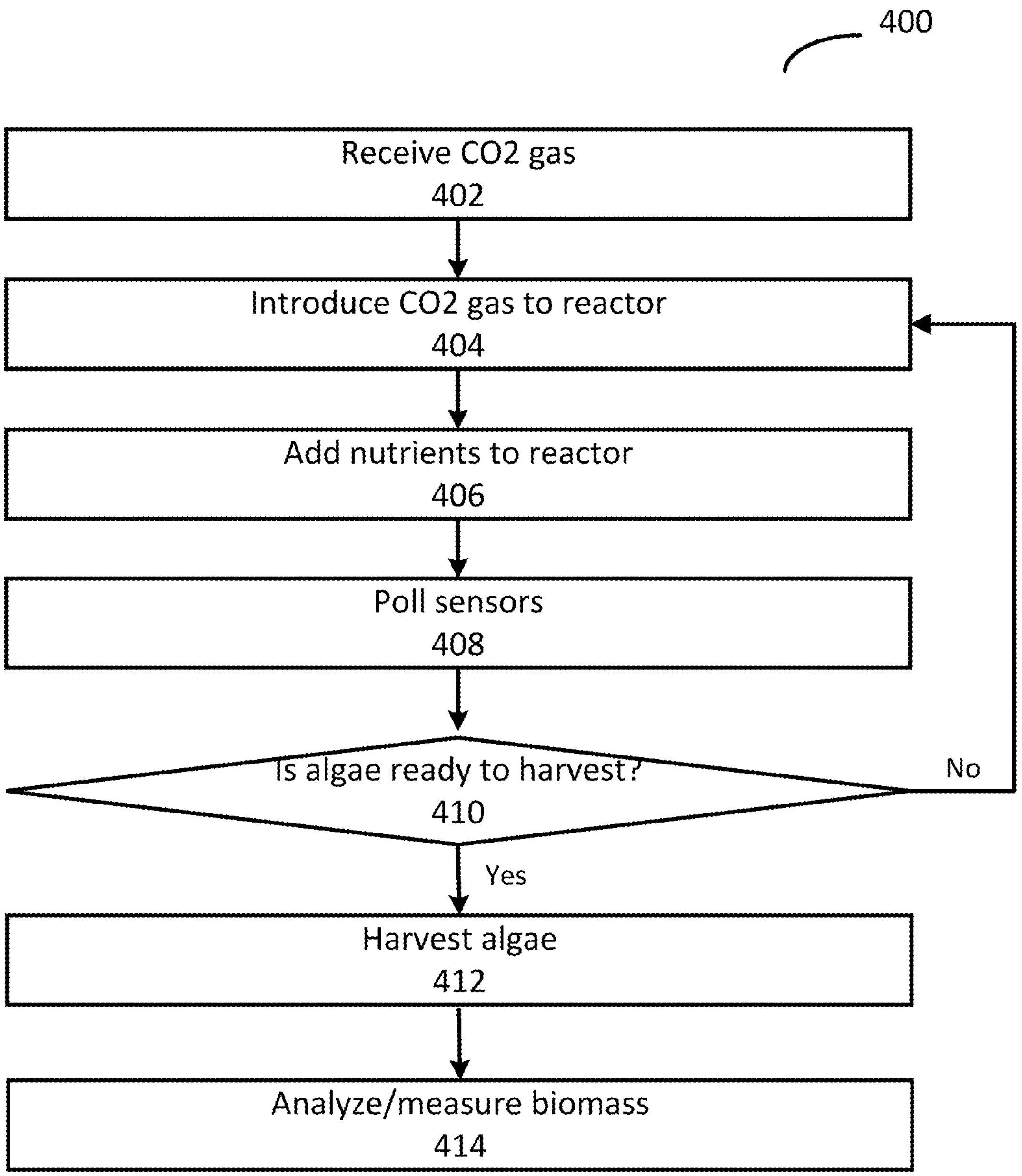
FIG. 4 is a flowchart illustrating an exemplary method of algae production.

FIG. 4 is a flowchart illustrating an exemplary method 400 of algae production. Method 400 may be performed based on execution of the production module 158 by controller 148. As noted herein, production module 158 may include algorithms and instructions executable to coordinate and control operations of algae reactor system 116 including the various components 118-130 thereof.

Method 400 may begin with step 402, in which a CO2-containing gas is provided to and received by algae reactor 116. The CO2-containing gas may be compressed or concentrated, such as which may result from a carbon capture system including a pressure swing cycle or temperature swing cycle process. In some implementations, the CO2-containing gas may include atmospheric gases in addition to an increased concentration of CO2 resulting from one or more industrial processes such as from an energy production facility utilizing combustion, concrete production plant, fermentation processes, metallurgy, etc.

At step 404, the CO2-containing gas may be added to one or more algae reactors 116. As noted above, the CO2-containing gas may be compressed such that the pressure is greater than atmospheric pressure. The pressure may further be sufficient to overcome the pressure of water and/or a semipermeable membrane, air stone, fluid/air barrier, etc., thereby allowing the CO2 to form bubbles within a growth medium such as water or an algae slurry that includes at least algae and water. In some embodiments, the CO2 may be introduced into water separate from the photobioreactor to allow the CO2 to solubilize into the water prior to being introduced into the photobioreactor. The pressure, flow rate, membrane pore size, etc., may be adjusted to achieve a desired bubble size and production rate to achieve agitation of the column of algae slurry and complete solubilization of the CO2 in the CO2-containing gas into the water.

At step 406, nutrients may be added to the reactor in accordance with one or more targets associated with algae growth, carbon capture, or combination thereof. Different nutrients and amounts thereof may be provided and adjusted based on real-time data captured by sensors 152 so as to create and/or maintain conditions associated with reaching the targets. In some implementations, artificial intelligence models and machine learning techniques may be used to correlate different conditions and associated actions or adjustments to the targeted growth or carbon capture.

At step 408, one or more sensors 152 may be polled. Each sensor 152 may be configured to quantify one or more characteristics and/or parameters of the algae reactor 116, which may include characteristics of the algae, such as the concentration of algae in the water growth medium, light penetration through the algae slurry, etc., environmental parameters, such as temperature, solubilized CO2 concentration, concentration of one or more nutrients, etc. In other embodiments, sensors 152 may measure parameters of the algae reactors such as the pressure and/or flow rate of a CO2-containing gas being introduced into the algae reactor 116, light intensity, etc.

At step 410, it may be determined whether the algae is ready for harvest. The algae may be ready for harvest based upon one or more parameters including any of the concentration of algae, light penetration through the algae slurry, slowed algae growth rate, etc. In an embodiment, the algae is ready for harvest, as the growth rate of the algae has begun to slow, and the penetration of light through the algae slurry is below 20%, where 100% is the amount of light penetration through water with no algae present.

At step 412, the algae may be harvested if the algae is ready to be harvested. The algae is harvested by drawing off at least some of the algae slurry from the algae reactor 116 and separating the water from the algae. Separating the algae may be done at least in part using a biomass membrane separator 134. In an embodiment, greater than 50% of the water is separated from the algae using a semipermeable membrane. The algae may further be dried using a biomass steam dryer to remove the remaining water from the biomass until no more than 5% remains. In alternate embodiments, a higher or lesser target moisture content may be used as required by the intended use. The intended use may be determined by a purchaser of the dried algae. Water separated from the algae may be collected and utilized elsewhere in the algae growth process or may alternatively be available as a product for sale. For example, collected water may be supplied to one or more customers, particularly if the region in which the water is collected is arid. In some embodiments, exhaust gases, such as oxygen produced by the algae, may be collected, and sold as a product. Collected exhaust gases, water, etc. may require further processing prior to being sold as a product.

At step 414, the algae biomass may be analyzed and measured to determine the amount of algae produced. Measuring the algae biomass may further include subtracting an initial amount of biomass including an algae culture 126 which provided the initial population of algae in the algae reactor 116. In an embodiment, the harvested algae biomass includes a first amount, which may include an explicit measured value such as 1500 kg.

In some implementations, the biomass may further be processed into different forms and incorporated into different end-products (e.g., as may be specified by automated workflows associated with different client entities, rules, parameters, transactions). In some embodiments, processing may include drying to a specific moisture content to be sold as a bulk algae product and may optionally be ground into a powder or other desired format. In some embodiments, the algae may be packaged as compacted pellets or bricks. Examples of uses for bulk algae may include for animal or fish feed or for human consumption. In other embodiments, algae may be processed into one or more component parts to be sold, such as carbohydrates, amino acids, lipids, or mineral content. Carbohydrates may be separated from algae via processes such as hydrolysis. Uses of carbohydrates extracted from algae may include use as feed supplements, raw material for fermentation, bio-fertilizer, etc. Amino acids may be separated from algae via methods such as those including the use of solvents or enzymes. Uses of amino acids extracted from algae may include nutritional supplements, cosmetics, pharmaceuticals, petrochemical feedstock, bio-fertilizer, pesticides, etc. Lipids may be separated from algae via processes such as solvent extraction, mechanical extraction, and solvent-free extraction. Uses of lipids extracted from algae may include animal or fish feed, cosmetics, pharmaceuticals, petrochemical feedstock for biofuels, etc. In some embodiments, processing may include steps intended to remove unwanted material which may include contaminants which may be biologic, such as bacteria, viruses, fungi, etc., chemical, such as residual concentrations of nutrients used as fertilizer, or physical, such as metal, plastic, glass, etc. which may have been introduced into the algae during the growth, harvest, and/or processing steps.

Figure 5:
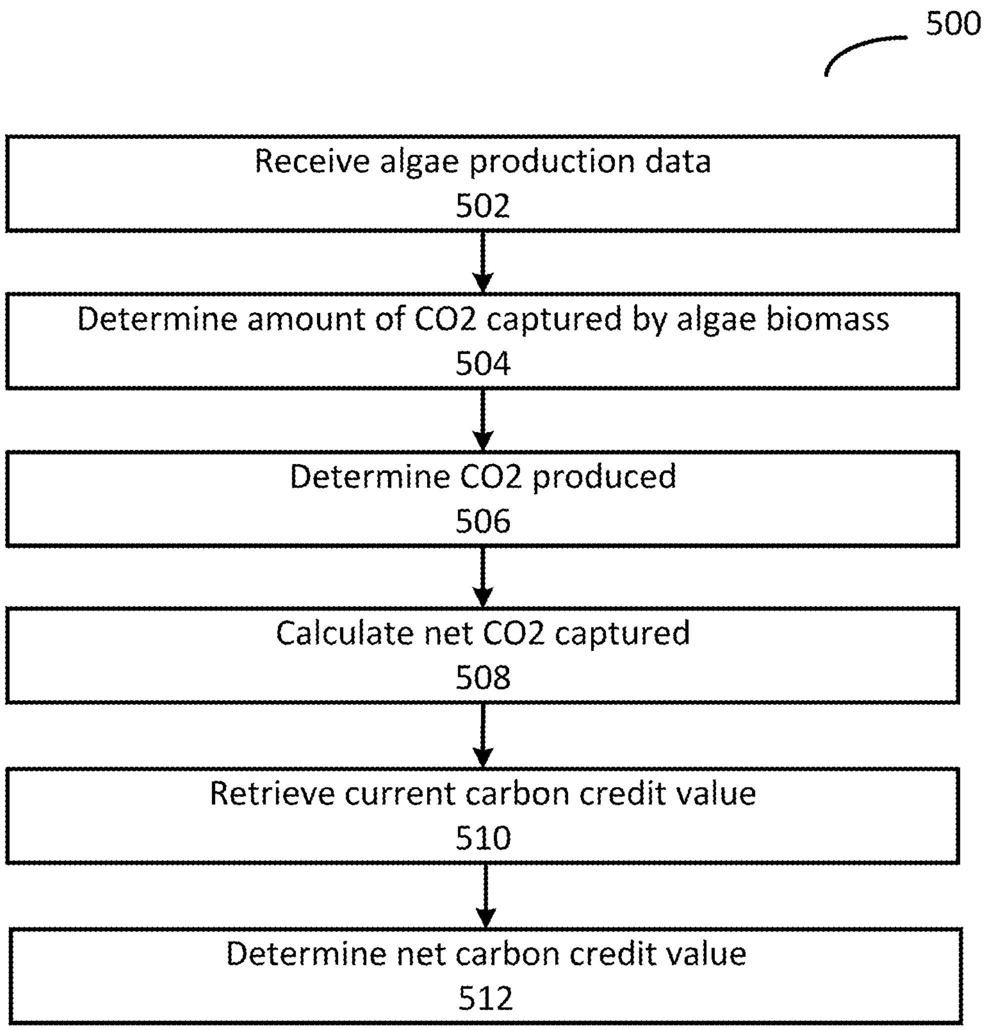
FIG. 5 is a flowchart illustrating an exemplary method of carbon credit analysis.

FIG. 5 is a flowchart illustrating an exemplary method 500 of carbon credit analysis. Method 500 may be performed based on execution of the carbon credit module 160 by controller 148. As noted herein, carbon credit module 160 may include algorithms and instructions executable to analyze the algae biomass produced by algae reactor system 116 and perform assessments as to associated carbon credits or other metrics.

Method 500 may begin with step 502, in which algae production data may be received regarding the biomass produced in at least one algae reactor 116. In an embodiment, the biomass including 1500 kg of algae dried to 5% water content. Such data may be based on one or more real-time measurements taken by sensors 152 monitoring the algae reactor 116.

At step 504, the amount of CO2 captured by the algae may be determined based on the received algae production data. This may be performed, for example, by querying a database, a third party network 142, or third party database 144, to determine ratios of the biomass weight to carbon dioxide captured. Under one exemplary set of conditions, algae may be considered to have consumed 1.83 g of CO2 to produce 1 g of biomass. The ratio of biomass weight to carbon dioxide captured may vary based upon the species of algae. For example, in another implementation, the algae may consume 2.7 g of CO2 to produce 1 g of biomass. In an embodiment, determining that the CO2 captured by a first amount of algae dried to 5% water content is equivalent to a first amount of CO2 which has been sequestered by the algae.

At step 506, it may be determined how much CO2 was produced and/or released as a result of producing the algae biomass. For example, CO2 may have been produced to generate the electricity used to power lights, pumps, heating and/or cooling, and other processes requiring electricity. In some processes, such as drying a CO2-containing gas and/or algae, combustion of organic matter and/or hydrocarbons may be utilized. The CO2 generated from these sources and/or processes may be directly offset by capturing the generated CO2 and processing the CO2 in the algae reactor. In other embodiments, the CO2 emitted from a power generation facility may be found via a third party network 142 and/or third party database 144 indicating the sources of electricity utilized by the algae reactor facility and their associated emissions. For example, a power company providing electricity for an algae reactor 116 may report their total electricity generation by source, from which the associated emissions may be calculated to achieve an average amount of CO2 emissions per unit of electricity, such as 400 kg of CO2 per megawatt-hour. The amount of CO2 produced may further include sources such as transportation. The CO2 produced may additionally include CO2 vented to atmosphere which was not solubilized in the water of the algae reactor 116 and consumed by the algae. In some embodiments, the CO2 produced may include fixed amounts, such as CO2 emitted from processes related to the manufacturing, transportation, and assembly of an algae reactor 116. In such embodiments, the CO2 produced may be determined by calculating the total CO2 generated from the manufacturing, transportation, and assembly of an algae reactor 116 and amortizing it over the expected operational life of the algae reactor 116. In an embodiment, the total amount of CO2 produced may include a fixed contribution and a variable contribution which is summed to include a total amount of CO2 produced.

At step 508, the net amount of CO2 captured may be calculated by offsetting or subtracting the amount of CO2 produced from the total amount of CO2 captured by the harvested algae biomass. In an embodiment, a first amount of CO2 is captured by the algae biomass harvested from an algae reactor 116, a total amount of CO2 was produced to capture the first amount of CO2, resulting in a net CO2 captured.

At step 510, the current values of one metric ton of CO2 as a carbon credit may be retrieved (e.g., from local or remote databases). The value of a carbon credit may be identified by querying one or more of a third party network 142 and/or third party database 144 such as may belong to a government agency or brokerage. In some embodiments, the carbon credit may be hosted on a local exchange. In an embodiment, the value of a carbon credit equal to one metric ton of CO2 is first amount as received from an exchange. Carbon credits may be determined by government agencies, laws, or may be dynamic, fluctuating based upon market factors such as supply and demand.

At step 512, the carbon credit value of the net CO2 captured may be determined. The net carbon credit value is determined by multiplying the net CO2 captured by the current carbon credit value. In an embodiment, the net CO2 captured is the net CO2 captured, and the current carbon credit value of one metric ton of CO2 is equal to a first amount as received from an exchange, which are multiplied to find the dollar value of the net CO2 captured. The value of net CO2 captured may be calculated in any currency utilizing an appropriate value received from an exchange utilizing the currency, or by using an exchange rate to convert to the desired currency. In an embodiment, the net carbon credit value for the net amount of CO2 captured by the algae reactor 116 may be the calculated dollar value of the net CO2 captured.

Figure 6:
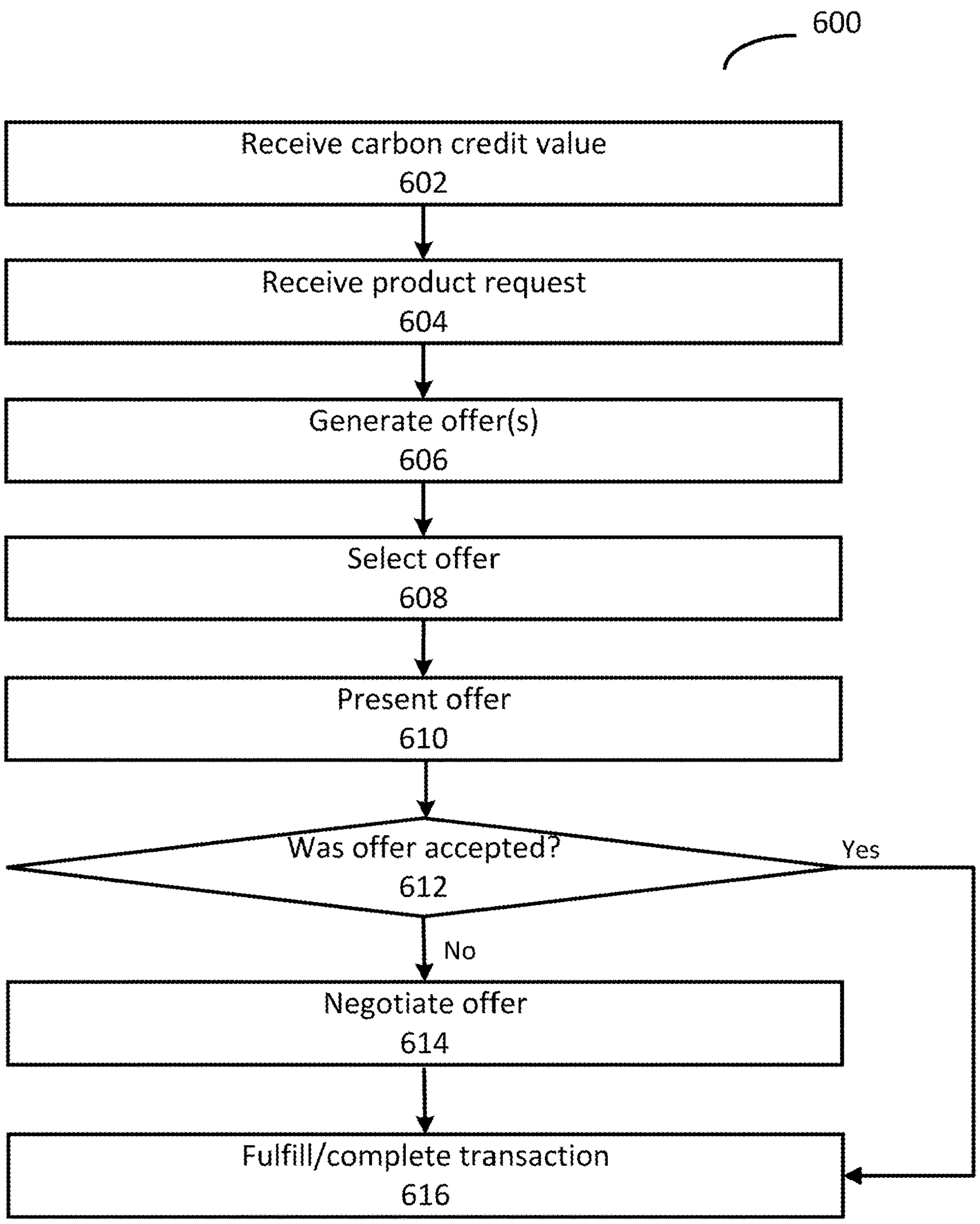
FIG. 6 is a flowchart illustrating an exemplary method of carbon credit brokerage and initiation of automated workflow.

FIG. 6 is a flowchart illustrating an exemplary method 600 of carbon credit brokerage and initiation of automated workflow. Method 600 may be performed based on execution of the brokerage module 162 by controller 148. As noted herein, carbon credit module 160 may include algorithms and instructions executable to select and initiate automated workflows associated with algae production based on carbon capture targets and associated rules and parameters.

Method 600 may begin with at step 602, in which a carbon credit value may be received from the operations module 154. In an embodiment, the carbon credit value is a calculated dollar value of the net CO2 captured by the algae reactor 116.

At step 604, a request for one or more products may be received. A product may be any of carbon credits, an algae product, water, oxygen, and any other product and/or service which may be related to an algae reactor. In some embodiments, a product request may include an inquiry, interest, or requested amount of carbon credits to be purchased as offsets. In another embodiment, a product request may include an algae product, such as dried algae, or an algae slurry. In another embodiment, the request may include one or more byproducts of a CO2 capture and algae growth and harvest process, such as water, oxygen gas, nitrogen gas, etc. In some embodiments, a request may include a request to purchase an algae reactor 116 system and/or license for capturing carbon dioxide. A request may instead include request for the installation of an algae reactor 116 to capture CO2 from one or more industrial processes such as combustion, concrete production, fermentation, metallurgical processes, etc. In an embodiment, receiving a request to install an algae reactor 116 at a coal power plant. A product request does not require initiative on the part of a customer, client, or requesting party, but instead may be a positive response or correspondence to marketing materials and/or sales outreach such as email or phone calls.

At step 606, one or more offers may be generated for the requested product and/or services. The offers may include one or more products and/or services related to an algae reactor and terms, including any of price, contract period, warranty and service, etc. In an embodiment, an offer may include a quantity of carbon credits or carbon offsets and a dollar value equivalent for a net amount of CO2 captured by the algae reactor 116, or a future amount to be captured over a designated period of time by one or more algae reactors 116. In another embodiment, an offer may include an amount of dried algae product to be purchased for a specified dollar amount. A dried algae product may include one or more of bulk algae, or derivative products resulting from the processing of algae including any of carbohydrates, amino acids, lipids, ash or minerals, etc. In another embodiment, an offer may include an amount of money in exchange for the installation and appropriate licenses to facilitate operation of an algae reactor 116 at a coal power plant.

At step 608, an offer may be selected from among a plurality of generated offers. The offer may be selected to optimize one or more of cost, operational efficiency, quantity of carbon credits generated, etc. The offer selection criteria may be based upon the product and/or service request and/or the required parameters requested by the customer and/or the interests of the seller. In an ideal embodiment, the selected offer is optimized to maximize the seller's profits while being accepted by the customer and achieving an acceptable level of customer satisfaction.

At step 610, an offer may be presented to a client or customer. The offer including at least a product and/or service and a price. The offer may further include terms and conditions. An offer may be in any form including verbal, written, electronic, etc. An offer may be made and/or presented by any relevant party such as the seller or the buyer. In some embodiments, the offer may be presented on an exchange, such as via a third-party network 142. In other embodiments, the exchange may be locally hosted or may be a physical location or event.

At step 612, it may be determined as to whether the offer was accepted. Acceptance may take any form indicating confirmation and/or agreement to accept the offer and enter a contract for products and/or services. Similar to presenting an offer, the acceptance may be in any form including verbal, written, electronic, etc. If the offer is accepted, the method may skip ahead to step 616. If the offer is not accepted, the method may proceed to step 614.

At step 614, an offer may be negotiated if the customer does not accept the presented offer. In some embodiments, the customer may be presented with a second offer, selected from the previously generated offers, which is different than the first offer. In another embodiment, the customer may provide a counteroffer. In a further embodiment, additional offers may be generated from which a second offer may be selected. In some embodiments, several iterations of offers may be exchanged before an agreement is achieved forming a contract.

At step 616, the terms of the contract defined by the offer and acceptance of the offer may be fulfilled in accordance with an associated automated workflow. Fulfillment may be performed in a single action, such as automatically processing shipment of a quantity of algae product. Alternatively, fulfillment may include the installation and/or operation of an algae reactor 116 over a period of time, such as months or years, to produce algae biomass under specified conditions and produce a product based on the algae-biomass. In other embodiments, fulfilling an accepted offer may be providing a license to use technology related to an algae reactor 116 such that fulfillment includes making no effort to take enforcement actions against the client to whom the license was granted. A contract status may indicate that the contract is pending, has been accepted but is awaiting fulfillment, has been completed, etc.

FIG. 7 illustrates an exemplary computing system 700 that may be used to implement an embodiment of the present invention. The computing system 700 of FIG. 7 may include one or more processors 710 and memory 720. Main memory 720 stores, in part, instructions and data for execution by processor 710. Main memory 720 can store the executable code when in operation. The system 700 of FIG. 7 may further include a mass storage device 730, portable storage device 740 (e.g., media drive), output devices 750, user input devices 760, a graphics display system 770, and peripheral devices 780.

The components shown in FIG. 7 are depicted as being connected via a single bus 790. However, the components may be connected through one or more data transport means. For example, processor unit 710 and main memory 720 may be connected via a local microprocessor bus, and the mass storage device 730, peripheral device(s) 780, portable storage device 740, and graphics display system 770 may be connected via one or more input/output (I/O) buses.

Mass storage device 730, which may be implemented with a magnetic disk drive or an optical disk drive, is a non-volatile storage device for storing data and instructions for use by processor unit 710. Mass storage device 730 can store the system software for implementing embodiments of the present invention for purposes of loading that software into main memory 720.

Portable storage device 740 operates in conjunction with a portable non-volatile storage medium, such as a floppy disk, compact disk or Digital video disc, to input and output data and code to and from the computer system 700 of FIG. 7. The system software for implementing embodiments of the present invention may be stored on such a portable medium and input to the computer system 700 via the portable storage device 740.

Input devices 760 provide a portion of a user interface. Input devices 760 may include an alpha-numeric keypad, such as a keyboard, for inputting alpha-numeric and other information, or a pointing device, such as a mouse, a trackball, stylus, or cursor direction keys. Additionally, the system 700 as shown in FIG. 7 includes output devices 750. Examples of suitable output devices include speakers, printers, network interfaces, and monitors.

Display system 770 may include a liquid crystal display (LCD) or other suitable display device. Display system 770 receives textual and graphical information, and processes the information for output to the display device.

Peripheral devices 780 may include any type of computer support device to add additional functionality to the computer system. For example, peripheral device(s) 780 may include a modem or a router.

The components contained in the computer system 700 of FIG. 7 are those typically found in computer systems that may be suitable for use with embodiments of the present invention and are intended to represent a broad category of such computer components that are well known in the art. Thus, the computer system 700 of FIG. 7 can be a personal computer, hand held computing device, telephone, mobile computing device, workstation, server, minicomputer, mainframe computer, or any other computing device. The computer can also include different bus configurations, networked platforms, multi-processor platforms, etc. Various operating systems can be used including Unix, Linux, Windows, Macintosh OS, Palm OS, and other suitable operating systems.

The functions performed in the processes and methods may be implemented in differing orders. Furthermore, the outlined steps and operations are only provided as examples, and some of the steps and operations may be optional, combined into fewer steps and operations, or expanded into additional steps and operations without detracting from the essence of the disclosed embodiments.

What is claimed is:

1. A method for operating algae photoreactors for capture of carbon dioxide, the method comprising:

receiving information regarding a request for an algae biomass product; and executing instructions stored in memory, wherein the instructions are executed by a processor to:

identify an automated workflow from among one or more automated workflows stored in memory each associated with a corresponding set of rules or parameters for processing algae biomass;

monitor one or more conditions within an algae reactor that includes the algae biomass;

adjust the one or more conditions within the algae reactor in accordance with the identified automated workflow;

determine that the corresponding set of rules or parameters of the identified automated workflow have been fulfilled;

initiate harvesting of the algae biomass within the algae reactor; and determine a net carbon credit value based on extracted real-time sensor data regarding a current flow of a gas mixture containing CO2 within the algae reactor.

2. The method of claim 1, wherein the automated workflow further includes obtaining an equipment lease for capturing the gas mixture through the algae reactor.

3. The method of claim 1, wherein the automated workflow further includes allowing the gas mixture containing CO2 to flow through the algae conversion apparatus reactor.

4. The method of claim 1, wherein the automated workflow further includes extracting the real-time sensor data regarding the gas mixture containing CO2 flowing through the algae reactor.

5. The method of claim 1, further comprising extracting the real-time sensor data regarding energy and nutrients of the gas mixture containing CO2 flowing through the algae reactor.

6. The method of claim 2, wherein the automated workflow further includes extracting equipment lease costs of capturing the gas mixture through the algae reactor.

7. The method of claim 1, further comprising determining a real-time carbon credit value of the algae biomass within the algae reactor.

8. The method of claim 1, wherein determining the net carbon credit value of the gas mixture containing CO2 includes analyzing the real-time sensor data and one or more real-time carbon credit values from a carbon credit database.

9. The method of claim 8, wherein analyzing the real-time sensor data and the real-time carbon credit values results in a carbon credit equivalent value, and wherein determining the net carbon credit value is further based on the carbon credit equivalent value and real-time data regarding one or more costs.

10. The method of claim 8, wherein the net carbon credit value corresponds to one or more of an entirety of the algae biomass, a part of the algae biomass, or a value-added chemical process involving the algae biomass in whole or in part.

11. A system for operating algae photoreactors for capture of carbon dioxide, the system comprising:

a communication interface that communicates over a communication network, wherein the communication interface receives information regarding a request for an algae biomass product; and a processor that executes instructions stored in memory, wherein the processor executes the instructions to:

identify an automated workflow from among one or more automated workflows stored in the memory each associated with a corresponding set of rules or parameters for processing algae biomass;

monitor one or more conditions within an algae reactor that includes the algae biomass;

adjust the one or more conditions within the algae reactor in accordance with the identified automated workflow;

determine that the corresponding set of rules or parameters of the identified automated workflow have been fulfilled;

initiate harvesting of the algae biomass within the algae reactor; and determine a net carbon credit value based on extracted real-time sensor data regarding a current flow of a gas mixture containing CO2 within the algae reactor.

12. The system of claim 11, wherein the automated workflow further includes obtaining an equipment lease for capturing the gas mixture through the algae reactor.

13. The system of claim 11, wherein the automated workflow further includes allowing the gas mixture containing CO2 to flow through the algae reactor.

14. The system of claim 11, wherein the automated workflow further includes extracting the real-time sensor data regarding the gas mixture containing CO2 flowing through the algae reactor.

15. The system of claim 11, wherein the processor executes further instructions to extract the real-time sensor data regarding energy and nutrients of the gas mixture containing CO2 flowing through the algae reactor.

16. The system of claim 11, wherein the automated workflow further includes extracting equipment lease costs of capturing the gas mixture through the algae reactor.

17. The system of claim 11, wherein the processor executes further instructions to determine a real-time carbon credit value of the algae biomass within the algae reactor.

18. The system of claim 11, wherein the processor determines the net carbon credit value of the gas mixture containing CO2 by analyzing the real-time sensor data and one or more real-time carbon credit values from a carbon credit database.

19. The system of claim 18, wherein the processor analyzes the real-time sensor data and the real-time carbon credit values to determine a carbon credit equivalent value, and wherein the processor executes further instructions to determine the net carbon credit value based on the carbon credit equivalent value and real-time data regarding one or more costs.

20. The system of claim 18, wherein the net carbon credit value corresponds to one or more of an entirety of the algae biomass, a part of the algae biomass, or a value-added chemical process involving the algae biomass in whole or in part.

21. A non-transitory, computer-readable storage medium, having embodied thereon a program executable by a processor to perform a method for operating algae photoreactors for capture of carbon dioxide, the method comprising:

receiving information regarding a request for an algae biomass product;

identifying an automated workflow from among one or more automated workflows stored in memory each associated with a corresponding set of rules or parameters for processing algae biomass;

monitoring one or more conditions within an algae reactor that includes the algae biomass;

adjusting the one or more conditions within the algae reactor in accordance with the identified automated workflow;

determining that the corresponding set of rules or parameters of the identified automated workflow have been fulfilled;

initiating harvesting of the algae biomass within the algae reactor; and determine a net carbon credit value based on extracted real-time sensor data regarding a current flow of a gas mixture within the algae reactor.

* * * * *